(12) United States Patent
Bushnell

(10) Patent No.: US 11,857,340 B1
(45) Date of Patent: Jan. 2, 2024

(54) WATCH HAVING ELECTRODES FOR PHYSIOLOGICAL MEASUREMENTS

(71) Applicant: Apple Inc., Cupertino, CA (US)

(72) Inventor: Tyler S. Bushnell, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 1310 days.

(21) Appl. No.: 16/250,961

(22) Filed: Jan. 17, 2019

Related U.S. Application Data

(60) Provisional application No. 62/733,014, filed on Sep. 18, 2018.

(51) Int. Cl.
| | | |
|---|---|---|
| *A61B 5/335* | (2021.01) | |
| *A61B 5/00* | (2006.01) | |
| *A61B 5/024* | (2006.01) | |
| *G06F 1/16* | (2006.01) | |
| *A61B 5/0205* | (2006.01) | |

(52) U.S. Cl.
CPC ............ *A61B 5/681* (2013.01); *A61B 5/0006* (2013.01); *A61B 5/0205* (2013.01); *A61B 5/02438* (2013.01); *A61B 5/335* (2021.01); *G06F 1/163* (2013.01); *A61B 2560/0468* (2013.01)

(58) Field of Classification Search
CPC .......... A61B 5/681; A61B 5/335; A61B 5/332
See application file for complete search history.

(56) References Cited

U.S. PATENT DOCUMENTS

| | | |
|---|---|---|
| 7,894,888 B2 | 2/2011 | Chan et al. |
| 10,702,184 B2 * | 7/2020 | Riordan ............... A61B 5/7225 |
| 11,291,401 B2 * | 4/2022 | Velo ....................... A61B 5/282 |
| 2016/0058375 A1 | 3/2016 | Rothkopf |
| 2018/0220972 A1 * | 8/2018 | Jeong ................... A61B 5/7445 |

FOREIGN PATENT DOCUMENTS

| | | |
|---|---|---|
| CN | 204945633 | 1/2016 |
| WO | WO 2017/084464 | 5/2017 |
| WO | WO 2018/129847 | 7/2018 |

* cited by examiner

*Primary Examiner* — George R Evanisko
(74) *Attorney, Agent, or Firm* — BAKERHOSTETLER

(57) ABSTRACT

A watch having electrodes for physiological measurements is disclosed. The watch can be provided with an enclosure configured to couple to a wristband. An electrode can be disposed on the enclosure. Processing circuitry can be disposed in the enclosure and configured to use the electrode to obtain multiple types of physiological measurements.

14 Claims, 4 Drawing Sheets

US 11,857,340 B1

WATCH HAVING ELECTRODES FOR PHYSIOLOGICAL MEASUREMENTS

CROSS-REFERENCE TO RELATED APPLICATIONS

This application claims the benefit of U.S. Provisional Application No. 62/733,014, entitled "WATCH HAVING ELECTRODES FOR PHYSIOLOGICAL MEASUREMENTS," filed Sep. 18, 2018, the entirety of which is incorporated herein by reference.

TECHNICAL FIELD

The present description relates generally to electronic wearable devices, and more particularly to, for example, a watch having electrodes for physiological measurements.

BACKGROUND

Wearable electronic devices, such as watches, fitness trackers, and other wrist-worn devices, can be attractive choices for users due to their portability, aesthetic appeal, or potential to provide new functionalities over traditional electronic products. Typically, wearable electronic devices include internal electronics, such as one or more processors, housed within an assembly containing one or more input/output (I/O) devices that interface externally with the user, such as a display, a sensor, or the like. Because of their portability and ability to be closely coupled to the user's body, wearable electronic devices are particularly attractive candidates for taking physiological measurements. However, practical constraints with existing wearable devices have thus far prevented them from offering many useful physiological measurement functions.

BRIEF DESCRIPTION OF THE DRAWINGS

Certain features of the subject technology are set forth in the appended claims. However, for purpose of explanation, several embodiments of the subject technology are set forth in the following figures.

DETAILED DESCRIPTION

Figure 1:
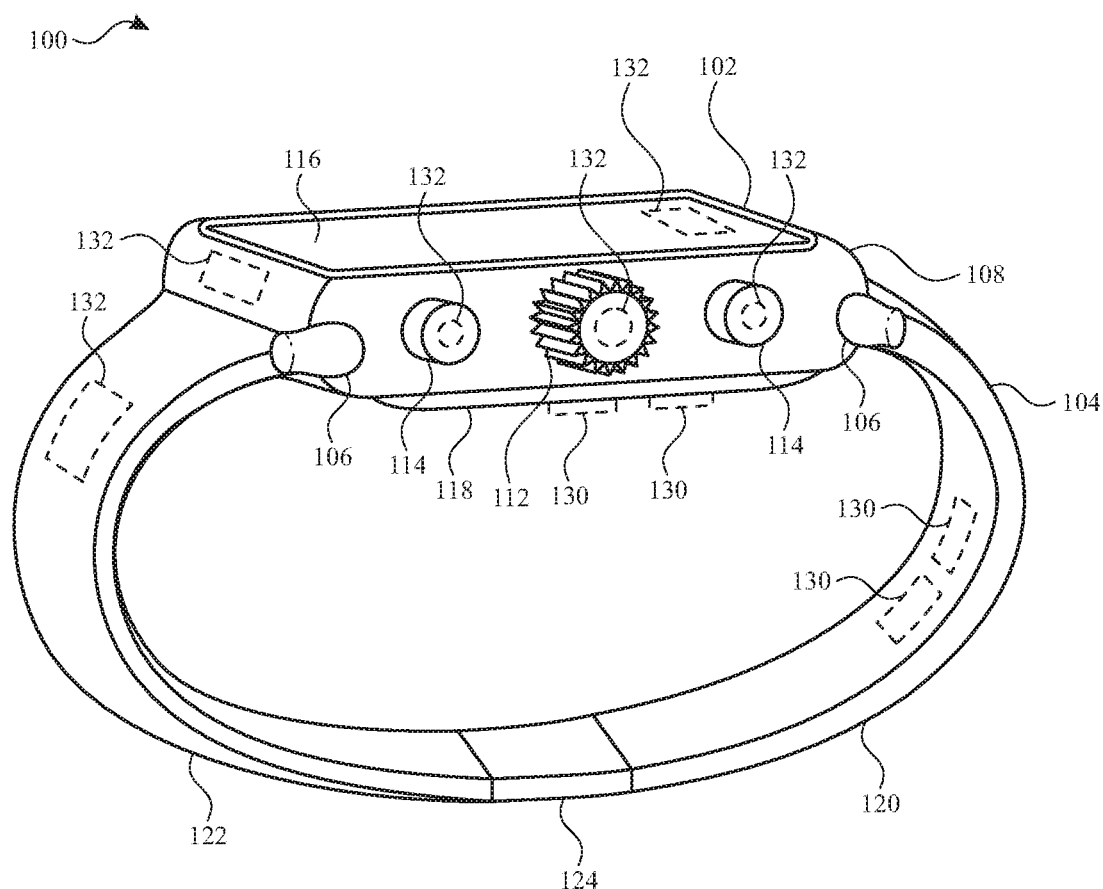
FIG. 1 is a perspective view of a watch, in accordance with some embodiments.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced without these specific details. In some instances, well-known structures and components are shown in block diagram form in order to avoid obscuring the concepts of the subject technology.

The following disclosure relates to an electronic wearable device, such as a watch or wrist-worn device. The wearable device can have electrodes capable of taking physiological measurements of a user when the device is worn on or otherwise coupled to a body of user. The placement or operation of the electrodes on the wearable device can, for example, allow for increased functionality in a relatively compact wearable device which may have limited real estate for functional components.

According to some embodiments, a wrist-facing surface of a watch enclosure or watch band can include a pair of electrodes implemented as surface contacts that contact the user's body when worn on the user's wrist, allowing the electrodes to take electrical measurements from the user's skin or otherwise take electrical measurements from the user's body. A pairing of the electrodes can be configured to obtain an electrical resistance measurement of the user's skin in order to determine a galvanic skin resistance (GSR), also sometimes referred to herein as a galvanic skin response. The pairing of electrodes can be implemented as wrist-facing electrodes that are formed using a conductive coating such as a physical vapor deposition (PVD) coating. The conductive coating can be formed on a non-conductive surface of the watch, such as a rear surface of back cover that is made from a non-conductive material. The electrodes formed from the conductive coating can provide for a relatively thin conductive component that can be patterned in a desired area to permit the coated electrodes to obtain suitable measurements from the user's body without unduly interfering with other operational components. For example, operational components such as optical and/or electromagnetic devices can be included in the wearable device and configured to interact with other external objects through or around the coated electrodes. In some embodiments, the conductive coating used to form the electrodes can also provide a cosmetic feature, which can allow the electrodes to provide a desired coloring or other external appearance while also providing for physiological measurement functionality.

According to some embodiments, one or more electrodes on the wearable device can be dual-purposed or multi-purposed for obtaining multiple types of physiological measurements. For example, to obtain a first type of measurement, an electrode on the wrist-facing surface can be operated in concert with another electrode on an outward-facing surface that faces away from the user's wrist. The electrode on the wrist-facing surface can provide a contact to the arm wearing the device, while other electrode on the outward-facing surface can provide a contact to the other free arm of the user by permitting the user to contact the outward-facing electrode with their other free arm. The electrodes coupled to the two arms can then cooperate to obtain an electrocardiogram (ECG or EKG) measurement based on an electrical potential difference between the two electrodes. When not in use for the ECG measurement, the wrist-facing electrode may then be operated for taking other physiological measurements, such as for a passive or continuous body monitoring scheme. By operating the same electrode for multiple measurements, e.g., both a ECG and GSR measurement, a need for one or more additional dedicated electrodes may be avoided and space may be saved on the wearable device.

These and other embodiments are discussed below with reference to FIGS. 1-9. However, those skilled in the art will readily appreciate that the detailed description given herein with respect to these Figures is for explanatory purposes only and should not be construed as limiting.

FIG. 1 is a perspective view of an example of an electronic device 100, such as a watch. While embodiments discussed herein are described with reference to a watch, it will be appreciated that the teachings relating to a watch can be applied to other electronic devices, including other wearable and/or portable computing devices. Examples include cell phones, smart phones, tablet computers, laptop computers, timekeeping devices, computerized glasses, headphones, head mounted displays, wearable navigation devices, sports devices, accessory devices, health-monitoring devices, medical devices, electronic bracelets and other jewelry. Hereinafter device 100 will be referred to as watch 100.

The watch 100 shown in FIG. 1 is implemented as a wrist-worn device having an enclosure 102 and a band 104. The band 104 is configured to wrap around a wrist of a user to secure the device in place on the user's body. The band 104 is coupled to the enclosure 102 to permit the enclosure 102 to be worn on the user's body together with the band 104.

With reference to FIG. 1, the enclosure 102 provides a structure that serves to enclose and support one or more internal components of the device, such as, for example, one or more integrated circuit chips, circuit boards, display devices, batteries, memory devices, or other functional components. It is contemplated that the enclosure can in general be implemented as any suitable structure that serves to enclose functional and/or operative components of the device, such as a watch, and that can be directly or indirectly coupled to the band 104 to permit the enclosure to be worn on the user's body. Although shown in FIG. 1 with a generally rectangular structure providing a rectangular front face, it is contemplated that the enclosure 102 can have any appropriate size or shape, such as round, hexagonal, square, or other shapes.

In some embodiments, for example as shown in FIG. 1, the enclosure 102 can provide main casing or casing assembly that provides an external structural framework of the watch 100 with which the user can directly interact. As shown in FIG. 1, the enclosure 102 can include a perimeter sidewall 108 adjoining a front cover 116 and a back cover 118. The front cover 116 can be disposed on a front side of the sidewall 108 and a front side of the enclosure 102, while the back cover 118 can be disposed on a back side of the sidewall 108 and the enclosure 102 that is opposite to the front side. Internal components can be disposed be disposed in an interior space between the front cover 116 and the back cover 118, while the sidewall 108 can extend peripherally or circumferentially around the interior space and internal components contained therein.

It is contemplated that the front cover 116, back cover 118, and sidewall 108 can each be made from discrete components or pieces that are attached or otherwise assembled together. Alternatively, it is contemplated that any two or more of the enclosure components can be integrally formed from a substantially monolithic structure to provide for the desired enclosure framework. It is also contemplated that any one of the front cover 116, the back cover 118, and the sidewall 108 can be made from multiple discrete pieces, layers, or other components that are attached or otherwise assembled together. In some embodiments, the enclosure 102 or any one or more parts of the enclosure 102 can be made from rigid materials. Examples of rigid materials that can be utilized for the enclosure 102 include glass, ceramics, crystalline materials such as sapphire, aluminum, steel, and/or plastics.

In some embodiments, for example as shown in FIG. 1, one or more external functional components such as input/output (I/O) devices can be included as part of the enclosure 102 or otherwise supported by or coupled to the enclosure 102 to allow for manipulation by or other interaction with a user. As used herein, "I/O device" refers to any user interface device configured to receive input from a user and/or provide output to a user. "Input device" as used herein refers to any user interface device configured to receive input from a user and which may or may not be configured to provide output. "Output device" as used herein refers to any user interface device configured to provide output to a user and which may or may not be configured to receive input. For example, the watch 100 can include one or more buttons 114 disposed externally on or as part of the enclosure 102. The buttons 114 can, for example, be implemented as mechanical push buttons or touch-sensitive buttons. Additionally or alternatively, the watch 100 can include a rotatable dial 112 disposed externally on or included as part of the enclosure 102. The rotatable dial 112 can be disposed rotatably with respect to the sidewall 108, and configured to provide for scrolling, sliding, or user interface (UI) navigation inputs. The button 114 and dial 112 are examples of I/O devices configured to interact with a user, and more particularly, are examples of input devices configured to receive input from a user for providing one or more functional inputs to the watch 100. It is contemplated that the I/O devices disposed on or supported by the enclosure can be positioned on the sidewall 108, as shown in FIG. 1, or positioned in any other suitable location on the enclosure.

With respect to the example shown in FIG. 1 and the frame of reference of a watch or wrist-worn device, the back cover 118 and back side correspond to a side of the enclosure 102 and the watch 100 that faces a wrist of the user when the watch 100 is worn on the wrist. More generally, the back cover 118 and the back side can face a body part of the user when the wearable device is worn on the body part. The front cover 116 and front side correspond to a side of the enclosure 102 and the watch that face away from the wrist of the user. More generally, the front cover 116 and the front side can face away from a body part of a user when the wearable device is worn on the body part. A display can be provided to present images or output various graphical information on or through the front cover 116 of the enclosure. In some embodiments, the front cover 116 can provide an input surface for a touch-sensitive device included in or overlapping with the display, such as a touch screen interface, force sensing device, and/or a fingerprint sensor. The input surface can, for example, permit a user to interact with graphical user interface (GUI) elements presented on the display. It is also contemplated that other wrist-worn devices can omit a display. Additionally or alternatively, it is contemplated that other I/O devices can be included, such as speakers, microphones, gesture interfaces, motion sensors, and the like.

The band 104 shown in FIG. 1 is implemented as a wristband that includes a first band strap 120 and a second band strap 122. The first band strap 120 and the second band strap 122 can connect to each other through a connector 124 that may, for example, be implemented as a clasp, a buckle, a magnetic attachment, or any other suitable mechanism for adjoining the first band strap 120 to the second band strap 122. Each of the first band strap 120 and the second band strap 122 can be made from any suitable flexible and/or rigid components that can generally conform to the outer surface of a user's wrist. Examples include, without limitation, leather, fabrics, rubber, nylon, plastics, and metallic bracelets. It is contemplated that the band 104 can be implemented in numerous different configurations and can generally include any suitable flexible or rigid components that can be removably wrapped around a wrist of a user. For example, in some embodiments the band 104 can omit the connector 124, such as an implementation having a single continuous watch band loop that is expandable to permit the expanded band 104 to be slid around a user's hand. Additionally or alternatively, the band 104 can include a sleeve or envelope that overlaps with the enclosure 102 in whole or in part to couple to the band 104 to the enclosure and hold the enclosure 102 in place. Various other configurations are possible. Likewise, while the band 104 is implemented as a wristband, it will be appreciated that the teachings of the watch band can be applied to other bands that are configured to wrap around other body parts of a user.

The attachment interface 106 shown in FIG. 1 includes multiple attachment points, and in particular, includes an attachment point on one edge of the enclosure 102 and another attachment point on an opposing edge of the enclosure 102 to connect the first band strap 120 to the enclosure 102 and the second band strap 122 to the enclosure, respectively. The attachment interface 106 can include, for example, a slot, a lug, a threaded fastener, or any other suitable component to connect the band 104 to the enclosure 102. Although multiple attachment points are shown in FIG. 1, it is contemplated that other implementations can utilize more attachment points or a single attachment point for connecting the band 104 to the enclosure 102. Although the attachment interface 106 is shown disposed on the sidewall 108 in FIG. 1, it is contemplated that the attachment interface 106 can disposed on or coupled to any other feasible location on the enclosure 102.

With continued reference to FIG. 1, the watch 100 can include one or more electrodes disposed on one or more exterior surfaces of the watch 100 to provide for physiological sensing functionality. The sensing electrodes can be disposed on one or more exterior surfaces of the watch 100, such as exterior surfaces of the watch enclosure 102 and/or band 104, to provide for a surface contact can take electrical measurements from the user's skin or body. The electrodes can be operated to perform an electrical measurement, for example, to measure electrocardiographic (ECG) characteristics, galvanic skin resistance, and other electrical properties of the user's body and/or the environment. It will be appreciated that any suitable number of electrodes can be provided. Each electrode can be insulated from other electrodes and/or other components of the watch. One or more electrodes can operate as a first terminal, and one or more electrodes can operate as an additional terminal. The electrodes can be of any suitable size, shape, and arrangement.

According to various embodiments, the sensing electrodes can include one or more wrist-facing electrodes 130, or more generally one or more body-facing electrodes disposed on a wrist-facing surface of the watch 100 or body-facing surface of the wearable device. As used herein, a "wrist-facing" surface or "wrist-facing" electrode refers to an exterior surface or electrode of a wrist-worn device that is configured to face towards or make contact with a wrist of a user when the wrist-worn device is worn on that wrist. Likewise and more generally, as used herein a "body-facing" surface or "body-facing" electrode refers to an exterior surface or electrode of a wearable device that is configured to face towards or make contact with a body part of a user when the wearable device is worn on that body part.

The precise location and orientation of a wrist-facing or body-facing surface with respect to the components of the wearable device can vary depending on the implementation, design, and construction of a particular device. With respect to the watch example shown in FIG. 1, the exterior surface of the back cover 118 that is disposed on the back side of the back cover 118 and faces away from an interior of the enclosure 102 is part of a wrist-facing surface of the watch 100. Likewise, the exterior surface of the band 104 that corresponds to the inner diameter of the watch band loop is part of the wrist-facing surface of the watch 100. FIG. 1 shows examples of wrist-facing electrodes 130 that can be disposed on the wrist-facing surface of the watch 100. For example, in some embodiments the watch 100 can include one or more electrodes disposed on the wrist-facing surface of the back cover 118 and/or one or more wrist-facing electrodes 130 disposed on the wrist-facing surface of the band 104. According to some embodiments, and as further described herein, one or more pairings of the wrist-facing electrodes 130 can be used to obtain one or more GSR signals based on a measurement of resistance between the pairing of electrodes.

According to some embodiments, the sensing electrodes can additionally include one or more outward-facing electrodes 132 disposed on an outward-facing surface of the watch 100 or wearable device. As used herein, an "outward-facing" surface or "outward-facing" electrode refers to an exterior surface or electrode of a wrist-worn device or other wearable device that is configured to face away from and not make contact with a wrist of a user or other body part of a user when the wrist-worn device or other wearable device is worn on that wrist or body part.

The precise location and orientation of an outward-facing surface with respect to the components of the wearable device can vary depending on the implementation, design, and construction of a particular device. With respect to the watch example shown in FIG. 1, the exterior surface of the front cover 116 that is disposed on the front side of the front cover 116 and faces away from an interior of the enclosure 102 is part of an outward-facing surface of the watch 100. The exterior surface of the sidewall 108, the rotatable dial 112, and the buttons 114 are also part of the outward-facing surface of the watch 100, as is the exterior surface of the band 104 that corresponds to the outer diameter of the watch band loop. FIG. 1 shows examples of outward-facing electrodes 132 that can be disposed on the outward-facing surface of the watch 100. For example, in some embodiments the watch 100 can include one or more outward-facing electrodes 132 disposed on the outward-facing surface of the enclosure 102 such as the outward facing electrodes 132 disposed on the sidewall 108, the front cover 116, and/or input devices such as the button(s) 114 and/or the rotatable dial 112. Additionally or alternatively, the watch can include one or more outward-facing electrodes 132 disposed on the outward-facing and outer diameter surface of the band 104.

Figure 2:
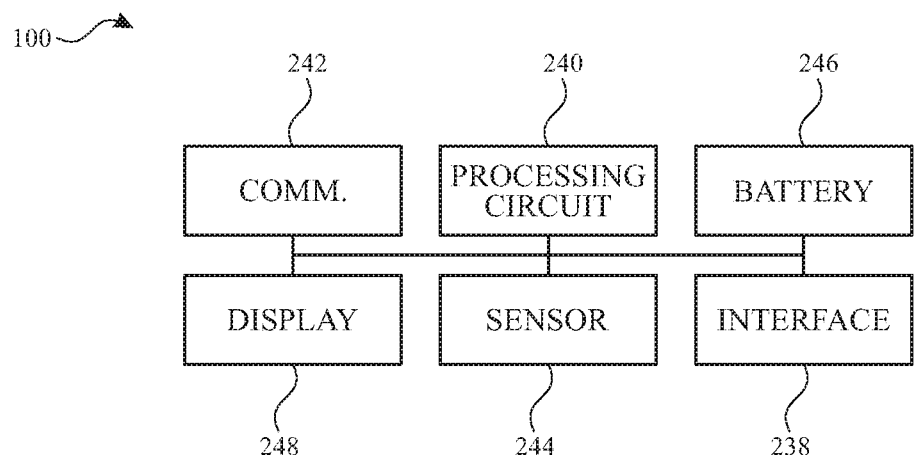
FIG. 2 is a block diagram of a watch, in accordance with some embodiments.

FIG. 2 shows a block diagram of watch 100 showing various functional components that may, for example, be housed within the enclosure 102. The watch 100 can further include one or more other user interfaces 238 for receiving input from and/or providing output to a user. For example, one or more buttons, dials, crowns, switches, or other devices can be provided for receiving input from a user. The user interface 238 can include a speaker, a microphone, and/or a haptic device. A haptic device can be implemented as any suitable device configured to provide force feedback, vibratory feedback, tactile sensations, and the like. For example, in one embodiment, the haptic device may be implemented as a linear actuator configured to provide a punctuated haptic feedback, such as a tap or a knock.

As further shown in FIG. 2, the watch 100 includes one or more processing circuit(s) 240 (referred to generally herein as processing circuitry) that is/are configured to perform one or more functions for the watch 100. By way of example, the processing circuitry can include one or more microprocessors, microcontrollers, field programmable gate arrays (FPGAs), application-specific integrated circuits (ASICs) such as I/O controller ICs, central processing units (CPUs), graphics processing units (GPUs), digital signal processors (DSPs), discrete circuit elements, or other suitably configured electronic circuitry or computing elements. The processing circuitry can include or be configured to access a memory having instructions stored thereon. The instructions or computer programs may be configured to perform one or more of the operations or functions described with respect to the watch 100. The processing circuitry 240 can be implemented as an electronic device capable of processing, receiving, or transmitting data, signals, or instructions. As described herein, the term "processing circuitry" is meant to encompass a single processor or processing unit, a single integrated circuit, multiple processors, multiple integrated circuits, multiple processing units, or other suitably configured computing element or elements. The memory can store electronic data that can be used by the watch 100. For example, a memory can store electrical data or content such as, for example, audio and video files, documents and applications, device settings and user preferences, timing and control signals or data for the various modules, data structures or databases, and so on. The memory can be configured as any type of memory. By way of example only, the memory can be implemented as random access memory, read-only memory, Flash memory, removable memory, or other types of storage elements, or combinations of such devices.

As further shown in FIG. 2, the watch 100 may include a communication component 242 that facilitates transmission of data and/or power to or from other electronic devices across standardized or proprietary protocols. For example, a communication component 242 can transmit electronic signals via a wireless and/or wired network connection. Examples of wireless and wired network connections include, but are not limited to, cellular, Wi-Fi, Bluetooth, infrared, RFID and Ethernet.

As further shown in FIG. 2, the watch 100 may also include one or more sensors 244, such as biosensors or physiological sensors, positioned substantially anywhere on the watch 100. The one or more sensors 244 may be configured to sense substantially any type of characteristic such as, but not limited to, images, pressure, light, touch, force, temperature, position, motion, and so on. For example, the sensor(s) 244 may be a photodetector, a temperature sensor, a light or optical sensor, an atmospheric pressure sensor, a humidity sensor, a magnet, a gyroscope, an accelerometer, and so on. In some examples, the watch 100 may include one or more health sensors. In some examples, the health sensors can be disposed on or configured to sense through a bottom surface of the watch 100, such as on or near the back cover 118. The one or more sensors 244 can include optical and/or electronic biometric sensors that may be used to compute one or more physiological characteristics. A sensor 244 can include a light source and a photodetector to form a photoplethysmography (PPG) sensor. Light can be transmitted from the sensor 244, to the user, and back to the sensor 244. For example, the back cover 118 or other part of the enclosure 102 can provide one or more windows (e.g., opening, transmission medium, and/or lens) to transmit light to and/or from the sensor 244. The optical (e.g., PPG) sensor or sensors may be used to compute various physiological characteristics including, without limitation, a heart rate, a respiration rate, blood oxygenation level, a blood volume estimate, blood pressure, or a combination thereof. One or more of the sensors 244 may also be configured to perform an electrical measurement using one or more electrodes, such as electrode(s) 130 and electrodes 132. The electrical sensor(s) may be used to measure electrocardiographic (ECG) characteristics, galvanic skin resistance, and/or other electrical properties of the user's body. Additionally or alternatively, a sensor 244 can be configured to measure body temperature, exposure to UV radiation, and other health-related information.

As further shown in FIG. 2, the watch 100 may include a battery 246 that is used to store and provide power to the other components of the watch 100. The battery 246 may be a rechargeable power supply that is configured to provide power to the watch 100. The watch 100 may also be configured to recharge the battery 246 using a wireless charging system using, for example, an electromagnetic device such as an inductive charging coil.

As further shown in FIG. 2, the watch 100 can include a display 248. The display can include, for example, a liquid crystal display (LCD) panel, an organic light-emitting diode (OLED), a microLED panel, projector device, or any other suitable electronic display technology or display panel. In some embodiments, the display 248 can be configured to present information relating to other components of the watch 100 as images, video, text, or other graphical information. For example, the display 248 can be configured to present an ECG graph, GSR information, a heart rate, or other information gathered with the sensor(s) 244. The various components shown in FIG. 2 can be coupled together or to the processing circuitry 240 via one or more busses, wireless communication links, or other interconnection technologies.

FIGS. 3-6 illustrate an example of usage and operation for a watch 100, in accordance with some embodiments. FIGS. 3-6 show an example in which the watch 100 is configured to obtain two different types of physiological signals, such as a GSR signal and a ECG signal, using one or more shared sensing electrodes. More particularly, in the example shown in FIGS. 3-6, one or more of the wrist-facing electrodes 130 is dual-purposed for both GSR and ECG measurements.

Figure 3:
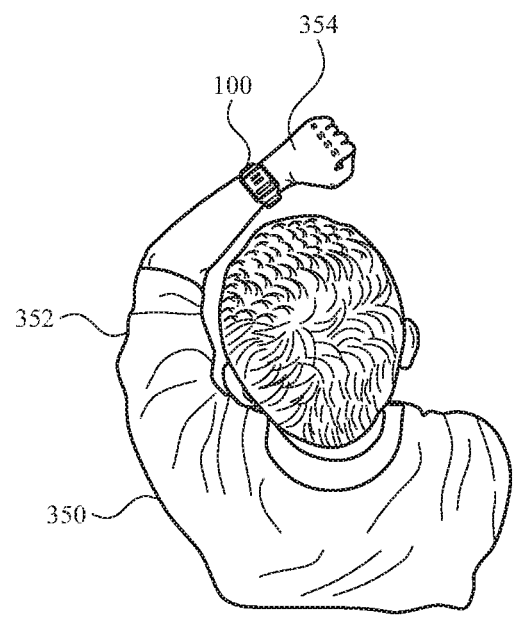
FIG. 3 is an illustration of a watch worn by a user during a physiological measurement, in accordance with some embodiments.

FIG. 3 shows a user 350 interacting with watch 100 during a first type of physiological measurement, such as a GSR measurement or a passive measurement that can be obtained from only the arm 352 wearing the device (left arm in the illustration). Referring to FIG. 3, the GSR signal can be obtained while the watch is worn on the user's wrist based on electrical coupling or ohmic contact between the wrist-facing electrodes 130 and the skin on the user's wrist 354. The measurement can be obtained without a need for the user to contact outward facing electrodes or other electrodes with another body part, such as their other free arm. Accordingly, in some embodiments the watch 100 can be configured to obtain the GSR measurement using a passive measurement scheme. As used herein, a "passive measurement" or obtaining a measurement or signal "passively" refers to obtaining the measurement or signal without providing an indication to the user that the measurement is being obtained. Alternatively, a passive measurement can be obtained with an indication, but performed automatically based on a continuous or intermittent sensing scheme, rather than in response to an active selection by the user 350.

Figure 4:
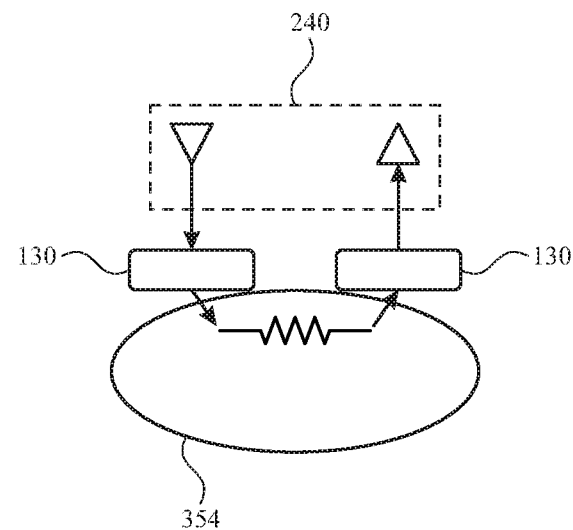
FIG. 4 is a schematic diagram of a watch taking the physiological measurement shown in FIG. 3, in accordance with some embodiments.

FIG. 4 is a schematic diagram showing an example of a drive and sense scheme that can be implemented by the processing circuitry 240 to perform the measurement and obtain the desired GSR signal during the user interaction shown in FIG. 3. As shown in FIG. 4, the GSR signal may be obtained by measuring a resistance between a pairing of the wrist-facing electrodes 130 when they are coupled to or in contact with the skin on the user's wrist 354. The pairing of electrodes may be spaced apart from one another and disposed sufficiently close to each other (for example within a millimeter or a few millimeters) to permit a resistance signal to be obtained within or across the skin. The measured resistance can be used to determine a resistivity of the user's skin, which can vary based on factors such as recent exercise, dry skin, arousal or other information indicative of an emotional state, or the like. To obtain the resistance measurement, the processing circuitry 240 can be configured to drive a drive signal onto a first wrist-facing electrode in the pairing of electrodes 130, and receive a sense signal onto a second wrist-facing electrode in the pairing. The drive signal can, for example, be a DC signal applied to the drive electrode, and the receive signal can be a response such as a current or voltage measured from the receive electrode. Additionally or alternatively, other sensing schemes such as other drive and sense schemes can be implemented, including, for example, drive signals involving time-varying signals or periodic waveforms.

Figure 5:
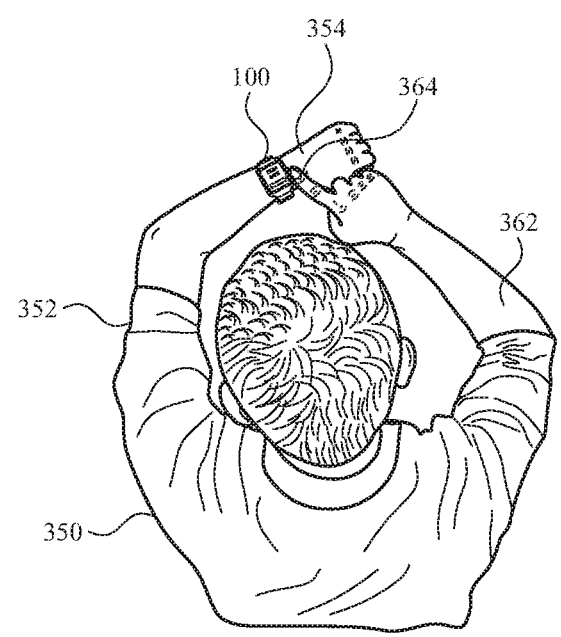
FIG. 5 is an illustration of a watch worn by a user during another physiological measurement, in accordance with some embodiments.

FIG. 5 shows a user 350 interacting with watch 100 during a second type of physiological measurement, such as an ECG measurement or an active measurement that can be obtained from both the arm 352 wearing the watch (left arm in the illustration) and the free arm 362 not wearing the watch (right arm in the illustration). Referring to FIG. 5, the ECG signal can be obtained while the watch is worn on the user's wrist 354 based on an electrical coupling or ohmic contact between the wrist-facing electrodes 130 and the skin on the user's wrist 354, and based on an electrical coupling or ohmic contact between the outward-facing electrodes 132 and the user's free arm 362, such as the skin on the user's finger 364. Based on the coupling or contact with the two arms, a voltage difference or potential difference resulting from depolarizations and repolarizations of the heart can be obtained.

In some embodiments, the ECG measurement can be an active measurement taken in response to a user selection to enter an ECG measurement mode, rather than a passive measurement like that described above for the GSR measurement. For the ECG measurement, the user may be prompted or instructed (e.g., using the interface 238 or display 248) to hold their finger or other portion of their arm on the outward-facing electrode 132, or the component of the device on which the outward-facing electrode 132 is disposed, for an extended period of time. This can permit the watch 100 (e.g., processing circuitry 240 of the watch) to obtain a series of ECG signals over time and generate a corresponding ECG graph that shows the electrical potential variation over time. The ECG graph can include various intervals, zones, or segments corresponding to a sinus rhythm of the heart, such as, for example, a PR interval, QT interval, PR segment, ST segment, or QRS segment. Those skilled in the art will readily appreciate the utility of ECG signals and the various portions in an ECG graph, and thus these intervals are not described here in detail. According to some embodiments, the processing circuitry can be configured to display the ECG graph on the display 248 or transmit the ECG graph to a doctor or other medical professional (e.g., using communication component 242).

Figure 6:
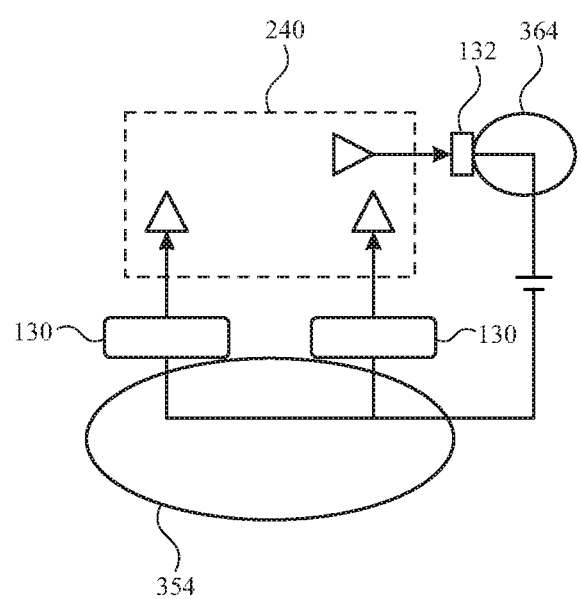
FIG. 6 is a schematic diagram of a watch taking the physiological measurement shown in FIG. 6, in accordance with some embodiments.

FIG. 6 is a schematic diagram showing an example of a drive and sense scheme that can be implemented by the processing circuitry 240 to perform the ECG measurement and obtain the desired ECG signal during the user interaction shown in FIG. 5. As shown in FIG. 6, the ECG signal may be obtained by measuring an electric potential difference between one or more of the wrist-facing electrodes (e.g., the first or second wrist-facing electrode 130 shown in the figure), and one or more outward-facing electrodes 132 (e.g., a third electrode 132 as shown in FIG. 6). One or more of the wrist-facing electrodes 130 used for the ECG measurement may be the same as that used in the GSR measurement described above with respect to FIGS. 3 and 4.

With continued reference to FIG. 6, the processing circuitry 240 can be configured to drive an outward-facing electrode 132 and receive a sense signal on both of the wrist-facing electrodes used during the GSR measurement. Alternatively, other implementations are contemplated in which only one sense signal is obtained from only one of the wrist-facing electrodes 130, or in which one or more of the wrist-facing electrodes 130 are driven with a drive signal during the ECG measurement and a sense signal is obtained from one or more outward-facing electrodes 132.

It is contemplated that the processing circuitry 240 can include or cooperate with a switch or switching device to obtain the GSR and ECG signals during distinct time periods. For example, during one time period, and in response to a user selection to obtain an ECG measurement, the common electrodes can be connected to or otherwise coupled with an ECG circuit or ECG receive circuit element to obtain the ECG signal while the outward-facing electrode 132 is being driven. When the ECG measurement is complete, the ECG circuit element can be decoupled from the shared electrode and repurposed for applying a drive signal or receiving a sense signal for a GSR measurement. Alternatively, other implementations are contemplated in which the different GSR signal and ECG signal are obtained simultaneously by obtaining a combined signal using a frequency coding or other coded multiplexing scheme. For example, in some embodiments, a first drive signal such as an ECG drive signal can be applied to the outward facing electrode 132 with a first frequency or other signal parameter. While the first drive signal is being applied, a second drive signal such as a GSR drive signal can be applied to one of the wrist-facing electrodes 130 (such as the left electrode shown in the figure), with a sufficiently different signal parameter such as a sufficiently different frequency to permit the constituent resulting signals to be discriminated or deconvolved from a combined sense signal. As used herein, "deconvolve" refers to any process for resolving, separating, or otherwise determining constituent components of a signal from a combined signal. The combined sense signal can be obtained from another one of the wrist-facing electrodes 130 (such as the right wrist-facing electrode shown in the figure)

while the distinct drive signals are applied and the processing circuitry 240 can be configured to discriminate or otherwise deconvolve the combined signal into a constituent GSR signal and ECG signal.

While only two wrist-facing electrodes 130 are shown in FIGS. 3-6, it is contemplated that more than two wrist-facing electrodes can be provided in various embodiments. For example, three, four, five, six, seven, eight, or any other suitable number of electrodes can be included to provide multiple distinct pairings of electrodes that can be used for determining multiple localized GSR signals or resistances between different respective pairings. This can be used, for example, to compensate for drift, mitigate against moisture on the skin or on the electrodes, or improve the measurement accuracy based on localized information that can be discriminated by using multiple resistances between multiple pairings of electrodes.

Figure 7:
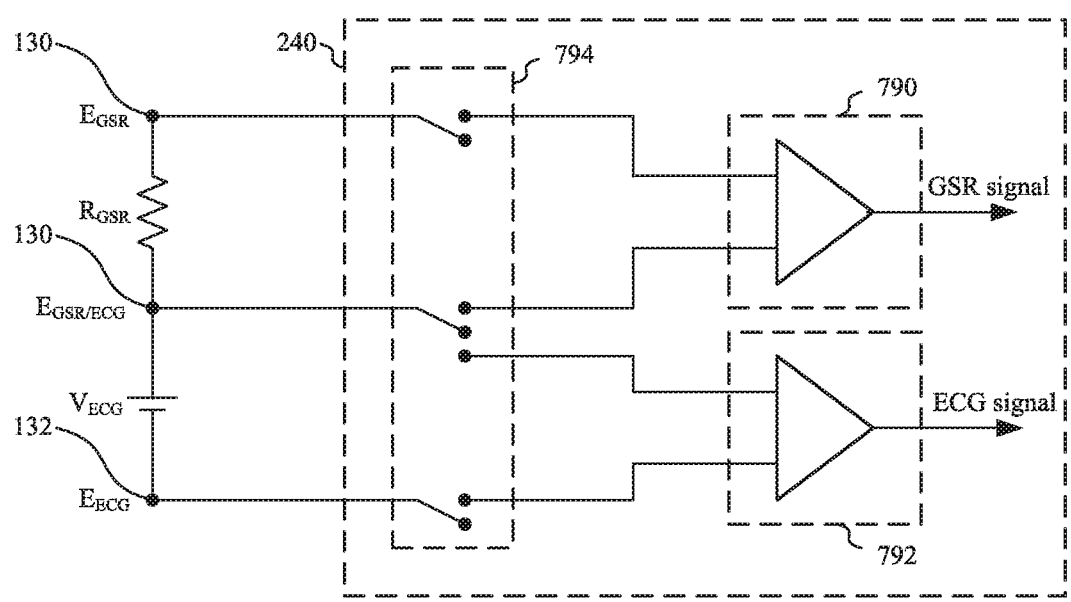
FIG. 7 is a circuit diagram of a watch configured to obtain physiological measurements, in accordance with some embodiments.

FIG. 7 shows an example of circuitry that can be utilized to obtain physiological measurements, in accordance with some embodiments. FIG. 7 is a circuit diagram showing circuit elements that can be implemented in the processing circuitry 240 and coupled to electrodes in the watch 100. FIG. 7 also shows some electrical properties of a user's body as equivalent circuit elements, such as $R_{GSR}$ corresponding to a resistance through a user's skin and $V_{ECG}$ corresponding to an electric potential between a user's arms and indicative of a polarization state of the user's heart. The example shown in FIG. 7 uses a switching configuration to permit a GSR signal and an ECG signal to be obtained from the same electrode during different time periods. Although only one shared electrode (labeled $E_{GSR/ECG}$) is shown in FIG. 7, the teachings of the circuit configuration shown in FIG. 7 can be applied to other configurations in which two or more electrodes are shared or multi-purposed for distinct types of measurements.

With reference to the example shown in FIG. 7, the processing circuitry 240 can include GSR sensing circuitry 790 having one or more circuits or circuit elements configured to obtain a GSR signal. It is contemplated that the GSR sensing circuitry 790 can include any of a variety of circuit elements suitable for obtaining a desired GSR signal indicative of a resistance $R_{GSR}$ between a pair of inward-facing electrodes 130. For example, the GSR sensing circuitry 790 can include one or more amplifiers, operational amplifiers (op-amps), filters, drivers, receivers, and/or other circuit elements configured to drive, receive, and/or process appropriate electrical signals onto and/or from the pairing of electrodes to take a GSR measurement.

With continued reference to the example shown in FIG. 7, the processing circuitry 240 can include ECG sensing circuitry 792 having one or more circuits or circuit elements configured to obtain an ECG signal. It is contemplated that the ECG sensing circuitry 792 can include any of a variety of circuit elements suitable for obtaining a desired ECG signal indicative of a potential difference $V_{ECG}$ between an inward-facing or wrist-facing electrode 130 and an outward-facing electrode 132. For example, the ECG sensing circuitry 792 can include one or more amplifiers, operational amplifiers (op-amps), filters, drivers, receivers, and/or other circuit elements configured to drive, receive, and/or process appropriate electrical signals onto and/or from the pairing of electrodes to take an ECG measurement.

The processing circuitry 240 can further include or otherwise cooperate with one or more switches 794 which are coupled between the sensing circuitry and one or more electrodes to selectively connect the electrode(s) to the corresponding sensing circuitry as appropriate. For example as shown in FIG. 7, the processing circuitry 240 can operate the switch(es) 794 to electrically connect inward-facing electrode 130 ($E_{GSR/ECG}$) to the ECG sensing circuitry 792 in order to obtain an ECG signal during a time period when an ECG measurement is desired. During another time period when a GSR measurement is desired and outside of the ECG measurement time period, the processing circuitry 240 can be configured to operate the switch(es) 794 to electrically disconnect the inward-facing electrode 130 ($E_{GSR/ECG}$) from the ECG sensing circuitry 792 and to electrically connect the inward-facing electrode 130 ($E_{GSR/ECG}$) to the GSR sensing circuitry 790.

It can be sufficient for a single switch 794 to be implemented between the sensing circuitry and a single shared electrode. Other implementations are contemplated in which multiple switches or other switching circuitry is implemented for selectively connecting multiple shared and/or unshared electrodes for electrically connecting and disconnecting them as desired during their respective sensing time periods. It is also contemplated that the GSR sensing circuitry 790 and the ECG sensing circuitry 792 can be entirely distinct or share one or more circuit elements in common, and it is sufficient for the switch 794 to be configured to selectively connect the shared electrode to any one or more circuit elements of the GSR sensing circuitry 790 and ECG sensing circuitry 792, respectively. Further, implementations are contemplated that omit the switching arrangement, such as embodiments that obtain and deconvolve a combined signal as described above, in which case a single set of sensing circuitry can be used for obtaining the combined measurement from the shared electrode(s).

Figure 8:
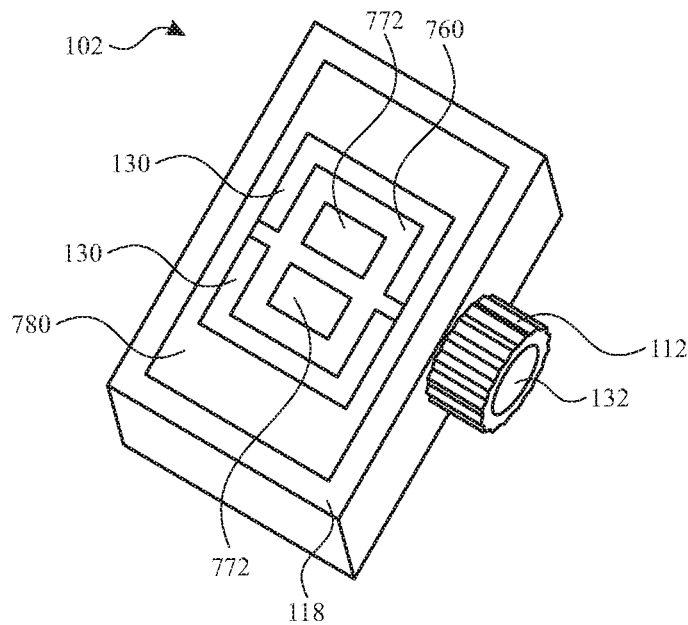
FIG. 8 is a perspective view of a watch enclosure, in accordance with some embodiments.
Figure 9:
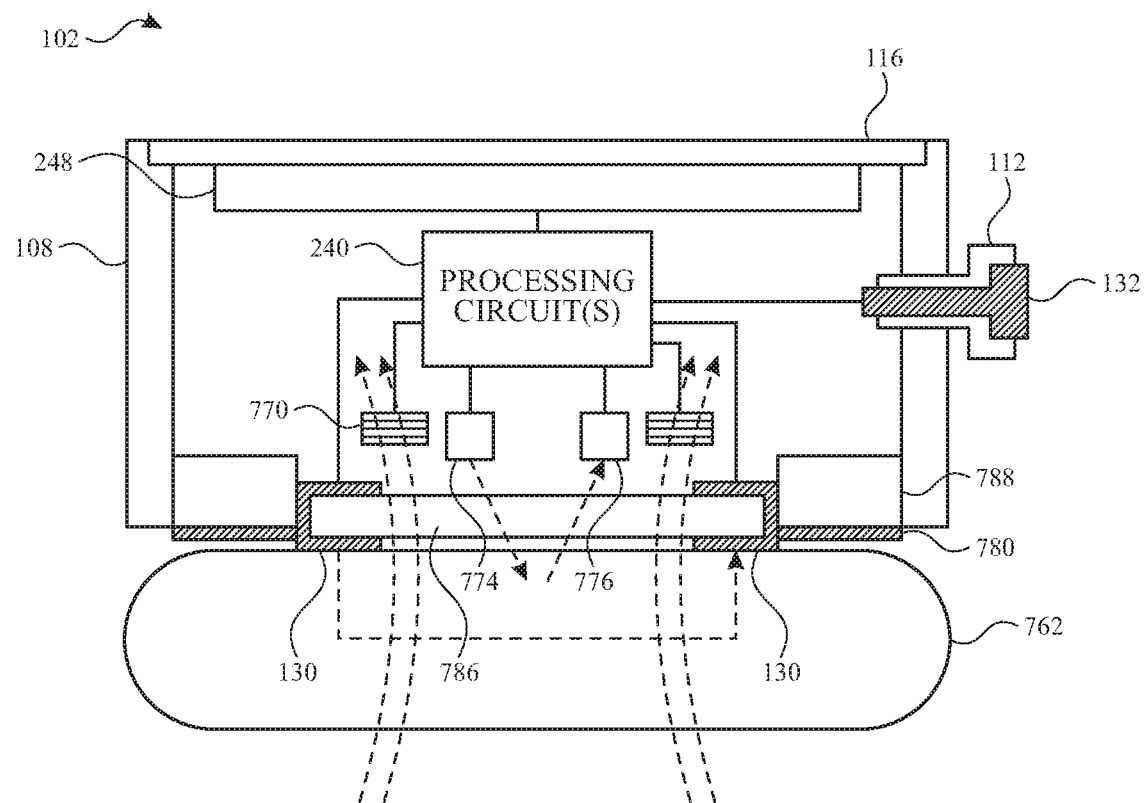
FIG. 9 is a sectional view of a watch enclosure, in accordance with some embodiments.

FIGS. 8 and 9 show an example of watch enclosure 102 in which physiological sensing electrodes such as wrist-facing electrodes 130 are formed using a conductive coating such as a physical vapor deposition (PVD) coating. FIG. 8 is a perspective view of an example of a watch enclosure 102 containing coated wrist-facing electrodes 130, while FIG. 9 is a cross section view of an example of an enclosure 102 containing coated wrist-facing electrodes 130.

The coated electrodes can be formed by coating a conductive material onto a non-conductive substrate. For example, a glass, sapphire, or ceramic substrate can be provided as the back cover 118, or a component of the back cover. Alternatively, other implementations are contemplated where the conductive coating material is formed on a surface of a dielectric layer that is formed on a conductive substrate, where the dielectric layer provides insulation to separate the electrodes or electrode channels from each other and from the conductive substrate.

Referring to FIGS. 8 and 9, the wrist-facing electrodes 130 can be formed by coating a PVD coating or other conductive material onto a back surface of the back cover 118 (bottom surface in the illustration of FIG. 9). The conductive coating can be advantageous for GSR electrodes that are configured to contact a wrist, for example, because the electrode layer or layers can be patterned in a desired area, such as a perimeter around a window 760, and/or made relatively thin to avoid interfering with other functional components of the watch that can be configured to interact with an external object or objects 762 through the back cover 118.

For example, in some embodiments, by having a thinner electrode layer (compared to, for example, an implementation using solid vias or solid contacts extending through the substrate) interference with flux lines interacting with an electromagnetic device 770 may be reduced. The electromagnetic device 770 can be disposed within the enclosure 102 and configured to interact with an external object 762 through the back cover and through or around the wrist-facing electrodes 130. For example, the electromagnetic device 770 can be implemented as an inductive charging coil used for charging the battery 246 and which interacts with an external object 762 (e.g., an external charging coil for the inductive charger) through the back cover 118. Flux lines travelling between the internal and external coils can thus be minimally interrupted based on the thin patterned electrode layer coated on the back surface of the back cover 118.

Additionally or alternatively, by patterning the wrist-facing electrodes 130 in a peripheral or perimeter area of the back cover or a component of the back cover, the wrist-facing electrodes 130 can be disposed around an optical window 760 that can permit light traveling through the back cover 118 from or to an optical device 772. For example, an optical device such as a PPG sensor or heart rate monitor can be disposed in the enclosure 102. The PPG sensor can include a light emitter 774 (e.g., a light emitting diode or other light emitter) configured to emit light to an external object 762 through the back cover and through the window 760 between the GSR electrodes. The PPG sensor can also include a light detector 776 (e.g., a photodiode or other photodetector), configured to detect a response of the emitted light through the back cover 118 and through the window between the GSR electrodes after the emitted light interacts with the external object 762 (e.g., a user's wrist). Although only one emitter and detector are shown in FIG. 9, it will be appreciated that the optical device can include any suitable number of emitters and or detectors, included multiple light emitters and or detectors in various embodiments.

According to some embodiments, the wrist-facing electrodes 130 used for GSR measurements can provide a cosmetic external layer (e.g., having a desired color for the external appearance of the device), alone or in connection with other non-functional cosmetic layers such as cosmetic layer 780. Additionally or alternatively, the conductive coating can be coated around an edge of a substrate such as an edge of the back cover 118 to provide electrode channels or routing that permits the coated wrist-facing electrodes 130 to electrically connect to processing circuitry 240 disposed in the enclosure 102.

FIG. 9 shows an example in which the back cover 118 is implemented with multiple discrete components, including a first inner component 786 and a second outer component 788. In this example, the wrist-facing electrodes 130 can be utilized for GSR measurements only, or one or more of the wrist-facing electrodes 130 can be dual purposed for both GSR and ECG electrodes.

Referring to FIG. 9, the wrist-facing electrodes 130 are coated on a back exterior surface of the inner cover component 786 (bottom surface in FIG. 8 facing away from an interior of the enclosure). The conductive coating material used for the wrist-facing electrodes 130 is also coated around an edge of the inner cover component and coated on a front interior surface of the inner cover component (top surface in FIG. 9 facing towards an interior of the enclosure). This permits the conductive coating material used for the wrist-facing electrodes 130 to electrically connect the electrodes on the exterior surface of the enclosure 102 to the processing circuitry 240 contained within the enclosure 102. As shown in FIG. 9, a complementary cosmetic coating (e.g., of the same color), can be disposed on the outer component 788. Numerous other arrangements are possible, including, for example, implementations in which functional GSR and or ECG electrodes are disposed on the outer cover component 788.

As described above, one aspect of the present technology is the gathering and use of data available from various sources to provide improved health-related or body monitoring functionality. The present disclosure contemplates that in some instances, this gathered data may include personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to diagnose heart conditions or determine an emotional state of a user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of diagnostic or health consultation services, the present technology can be configured to allow users to select to "opt in" or "opt out" of participation in the collection of personal information data during registration for services or anytime thereafter. In another example, users can select not to provide health or mood-associated data for targeted content delivery services. In yet another example, users can select to limit the length of time health or mood-associated data is maintained or entirely prohibit the development of a baseline health or mood profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, electrodes can be operated or physiological measurements can be obtained based on non-personal information data or a bare minimum amount of personal information, such as the content being requested by the device associated with a user, other non-personal information available to the device, or publicly available information.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A watch comprising:
an enclosure configured to couple to a wristband and comprising a sidewall and a back cover disposed on a back side of the sidewall;
a rotatable dial coupled to the sidewall;
a first electrode disposed on the back cover of the enclosure;
a second electrode disposed on the back cover of the enclosure;
a third electrode disposed on the rotatable dial; and
processing circuitry disposed in the enclosure and configured to use the first electrode and the second electrode to calculate a galvanic skin resistance signal and use the first electrode and the third electrode to calculate an electrocardiogram signal.

2. The watch of claim 1, further comprising:
a switch;
galvanic skin resistance sensing circuitry; and
electrocardiogram sensing circuitry,
wherein the processing circuitry is further configured to operate the switch to connect the first electrode and the second electrode to the galvanic skin resistance sensing circuitry during a first time period and connect the first electrode and the third electrode to the electrocardiogram sensing circuitry during a second time period.

3. The watch of claim 1, wherein the processing circuitry is further configured to obtain a combined signal from the first electrode, the second electrode, and the third electrode using a coded multiplexing scheme and determine the galvanic skin resistance signal and the electrocardiogram signal by deconvolving the combined signal.

4. The watch of claim 3, wherein the processing circuitry is further configured to:
drive a first drive signal onto the second electrode with a first signal parameter;
drive a second drive signal onto the third electrode with a second signal parameter different from the first signal parameter;
receive a combined sense signal from the first electrode, the combined sense signal including a response to the first drive signal and the second drive signal; and
deconvolve the combined sense signal to determine the galvanic skin resistance signal and the electrocardiogram signal.

5. The watch of claim 1, wherein the processing circuitry is further configured to:
receive a user selection; and
calculate the electrocardiogram signal in response to the user selection and calculate the galvanic skin resistance signal passively outside of a time period when the electrocardiogram signal is calculated.

6. The watch of claim 1, wherein the processing circuitry is configured to:
calculate the galvanic skin resistance signal by measuring an electrical resistance between the first electrode and the second electrode; and
calculate the electrocardiogram signal by measuring an electrical potential difference between the first electrode and the third electrode.

7. The watch of claim 1, wherein the processing circuitry is further configured to:
drive the first electrode or the second electrode and sense on the first electrode or the second electrode to calculate the galvanic skin resistance signal.

8. The watch of claim 1,
wherein the sidewall has a front side and a non-conductive back cover disposed on the back side,
wherein the first electrode comprises a conductive material coated on a back surface of the non-conductive back cover.

9. The watch of claim 8, wherein the conductive material is further coated around an edge of the non-conductive back cover.

10. The watch of claim 8, further comprising:
an electromagnetic device disposed within the enclosure and configured to receive a flux around the first electrode.

11. The watch of claim 8,
wherein the second electrode is coated on the back surface of the non-conductive back cover and spaced apart from the first electrode, the watch further comprising:
a window disposed between the first electrode and the second electrode; and
an optical device disposed within the enclosure and configured to emit or detect light through the window.

12. The watch of claim 1,
wherein the enclosure comprises a wrist-facing surface and an outward-facing surface,
wherein the first electrode and the second electrode are disposed on the wrist-facing surface,
wherein the third electrode is disposed on the outward-facing surface.

13. A watch comprising:
an enclosure having a first exterior surface, and second exterior surface, and an attachment interface configured to couple to a wristband;
a first electrode and a second electrode each formed of a conductive material coated on the first exterior surface;
a rotatable dial extending from the second exterior surface;
a third electrode disposed on the rotatable dial; and
processing circuitry disposed in the enclosure and configured to determine a resistivity of an object coupled between the first electrode and the second electrode, the processing circuitry further configured to use the third electrode and either first electrode or the second electrode to calculate an electrocardiogram signal.

14. The watch of claim 13,
wherein the enclosure comprises a sidewall and a back cover, wherein the back cover has a front side and a back side opposite to the front side, wherein the back cover is disposed on the back side and configured to face a wrist of a user when the enclosure is worn on the wrist, wherein the back cover has a front surface facing an interior of the enclosure and a back surface facing away from the interior of the enclosure, and wherein each of the first electrode and the second electrode comprises a physical vapor deposition coating on the back surface of the back cover.

\* \* \* \* \*